United States Patent [19]

Jonsson et al.

[11] 4,066,408
[45] Jan. 3, 1978

[54] CHROMOGEN-REACTIVE-INDICATOR PREPARATIONS CONTAINING A 3,3'-DI(CARBONYLOXY- OR SULFONYLOXY-GROUP-CONTAINING) BENZIDINE DERIVATIVE CHROMOGEN

[75] Inventors: Nils Åke Jönsson, Solna; Ferenc Merényi; Lars-Erik Westlund, both of Taby, all of Sweden

[73] Assignee: AB Kabi, Stockholm, Sweden

[21] Appl. No.: 766,961

[22] Filed: Feb. 9, 1977

Related U.S. Application Data

[63] Continuation-in-part of Ser. No. 515,195, Oct. 16, 1974, Pat. No. 4,008,267, which is a continuation-in-part of Ser. No. 118,531, Feb. 24, 1971, Pat. No. 3,859,341.

[51] Int. Cl.² ............ G01N 21/06; G01N 31/22
[52] U.S. Cl. ............................. 23/230 R; 23/230 B; 23/253 TP; 195/103.5 R; 195/103.5 C; 252/408
[58] Field of Search ............. 23/230 R, 253 TP; 252/408; 195/103.5 C

[56] References Cited

U.S. PATENT DOCUMENTS

| | | | |
|---|---|---|---|
| 3,290,228 | 12/1966 | Gretton | 23/253 TP |
| 3,298,789 | 1/1967 | Mast | 23/253 TP |
| 3,350,278 | 10/1967 | Gretton | 23/253 TP X |
| 3,453,180 | 7/1969 | Fraser | 23/253 TP X |
| 3,654,179 | 4/1972 | Bauer | 252/408 |
| 3,791,988 | 2/1974 | Josef | 252/408 |
| 3,814,668 | 6/1974 | Blake | 195/103.5 C |
| 3,964,871 | 6/1976 | Hochstrasser | 23/253 TP |

*Primary Examiner*—Sidney Marantz
*Attorney, Agent, or Firm*—A. A. Orlinger

[57] ABSTRACT

An analytical test, color change reagent preparation comprising peroxidase, an oxygen-oxidoreductase specific to a particular substance to be tested and a chromogen-reactive-indicator formula selected from (a) those having the general formula

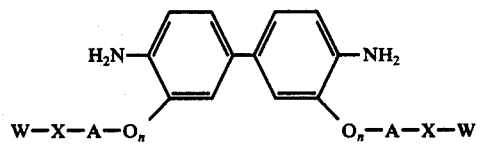

wherein X is the divalent carbonyloxy or sulfonyloxy group, W is hydrogen or another cation compatible with the aforesaid other ingredients of said reagent preparation, the subscript $n$ is 0 or 1, and (i) when X is the carbonyloxy group, A is a divalent alkylene chain with from 2 to about 7 carbons, and (ii) when X is the sulfonyloxy group, $n$ is 0 when A is the divalent alkylene chain of from 2 to about 7 carbons, and $n$ is 1 when A is straight chain trimethylene or tetramethylene, and (b) the acid addition salts of said disubstituted benzidine derivative, compatible with the aforesaid ingredients of the chromogen-reactive-indicator, when X is the carbonyloxy group.

The reagent preparations may be used in assaying organic substances such as sugars, uric acid, an amino acid and pyridoxaminophosphate.

18 Claims, No Drawings

CHROMOGEN-REACTIVE-INDICATOR PREPARATIONS CONTAINING A 3,3'-DI(CARBONYLOXY- OR SULFONYLOXY-GROUP-CONTAINING) BENZIDINE DERIVATIVE CHROMOGEN

This application is a continuation-in-part of copending application Ser. No. 515,195 filed Oct. 16, 1974, now U.S. Pat. No. 4,008,267 issued Feb. 15, 1977, which is a continuation-in-part of the then copending with it application Ser. No. 118,531 filed Feb. 24, 1971, now U.S. Pat. No. 3,859,341 issued Jan. 7, 1975.

This invention is that of a new class of chromogen-reactive-indicator compositions which include as their chromogen-reactive-indicator any of the class of stable compounds which are 3,3'-disubstituted benzidine derivatives. More specifically these compounds are benzidine having at both the 3- and 3'-positions the substituent group $-O_n-A-X-W$, wherein the subscript $n$ is 0 or 1, $A$ is a divalent lower alkylene chain with from 2 and beneficially 3 to about 7 carbons, $X$ is the carbonyloxy group

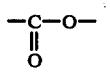

or the sulfonyloxy group

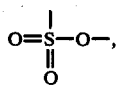

and $W$ is hydrogen or other chromogen-reactive-indicator compatible cation (as hereinafter defined) such as an alkali metal as sodium or potassium.

These 3,3'-disubstituted benzidine derivatives are primarily stable chromogens. They include also their chromogen-reactive-indicator compatible acid addition salts (as hereinbelow defined) of the derivatives wherein X is the carbonyloxy group, for example, their hydrogen halogenic acid addition salts such as their di-hydrohalides with any of the hydrogen halides as hydrobromic, hydrofluoric, or hydriodic acid, and particularly hydrochloric acid as in the di-hydrochloride salt of the 3,3'-disubstituted benzidine derivative, their hydrogen sulfates (from the use of sulfuric acid), or the sulfonates such as provided by use of a water-soluble lower alkyl sulfonate as methane sulfonic acid or ethane sulfonic acid, or of an aryl sulfonic acid as mononuclear such acid as phenylsulfonic acid and toluenesulfonic acid, and a binuclear such acid as naphthalene sulfonic acid.

These 3,3'-disubstituted benzidine derivatives (including any of these acid addition salt of any of them) are useful as the oxidizable chromogen constituent of a chromogen-reactive-indicator composition which in addition to the chromogen comprises peroxidase and an oxygen-oxidoreductase, for example, specific to a particular organic substance, the presence of which is to be tested for and for which there exists a specific oxygen-oxidoreductase, for example, an amino acid, uric acid, pyridoxaminephosphate, or a sugar to be tested for, such as glucose oxidase or galactose oxidase. Such reactive-indicator composition is used in the well known analytical method wherein hydrogen peroxide forms during the analytical reaction and serves to act on the oxidizable chromogen (that is to say, in its reduced state) to convert it to the oxidized state wherein it provides a visible color change in the presence of the particular substance such as a sugar or other of these organic substances being tested for.

The resulting chromogen-reactive-indicator compositions of the invention contain as their chromogen constituent a 3,3'-disubstituted benzidine derivative (or acid addition salt of those wherein X is the carbonyloxy group) of the class described in the second and third paragraphs of this specification. Another part of the invention is the use of these chromogen-reactive-indicator compositions in an analytical procedure applied, for example, to a sugar by use of such chromogen-reactive-indicator composition as in the qualitative or quantitative detection of such a sugar as glucose or galactose, or of such substances as referred to in the preceding paragraph.

In a number of such analytical methods wherein hydrogen peroxide is formed during the analytical reaction the hydrogen peroxide acts on a suitable chromogen compound which in its reduced state does not absorb light in the visible range of the spectrum, to convert the chromogen to its oxidized state which does absorb visible light.

Such analytical methods are used, for example, in the assay of such an organic substance for which a specific oxygen-oxidoreductase exists, as in the assay of individual sugars such as glucose, galactose, wherein an oxidase specific for the sugar involved, that is to say, an oxygen-oxidoreductase such as glucose oxidase or galactose oxidase, acts solely on the type of sugar to be determined, with formation of hydrogen peroxide. The latter under the influence of peroxidase enzyme, that is hydrogen-peroxide-oxidoreductase, oxidizes the chromogen compound with change of color proportionate to the concentration of the sugar.

The briefly earlier above used nomenclature including the term "oxidoreductase" is in accordance with the Enzyme Commission Classification System. Accordingly, Thomas E. Burman's "Enzyme Handbook", Springer-Verlag, Berlin, Heidelberg, New York, 1969, shows that all enzymes taking part in any redox-process are called oxidoreductases. Those which catalyze the reaction wherein oxygen is an electron acceptor are called oxygen-oxidoreductases. Those which catalyze reactions wherein hydrogen peroxide is an electron acceptor are called hydrogen-peroxide-oxidoreductases.

Other similarly behaving analyses are, for example, the determination of (i) uric acid with the use of uricase, or (ii) an amino acid with the aid of the corresponding amino acid oxidase, or (iii) pyridoxaminephosphate by pyridoxaminephosphate oxidase.

Chromogen-reactive-indicators are well known in the art by their inclusion as the color change indicating constituent or chromogen in chromogen-reactive-indicator compositions widely used, for example, to impregnate test strips such as those reactive-indicator compositions comprising peroxidase, an oxidizable chromogen forming a differently colored oxidation product in the presence of the peroxidase, and an oxidase specific, for example, to a particular sugar such as glucose of galactose being tested for, as illustrated in the Arne Lennart Dahlqvist U.S. Pat. No. 3,598,704 and below.

Thus, the earlier above mentioned chromogen-reactive-indicator compatible cation is one other than hydrogen which, when present as the carboxylate- or sulfonate-forming cation in a 3,3'-disubstituted benzidine derivative of the invention, is compatible with, by being inert to, the hydrogen peroxide, the peroxidase, and the further enzyme as the oxygen-oxidoreductase, such as glucose oxidase or galactose oxidase, or uricase, pyridoxaminephosphate oxidase, or amino acid oxidase, included in the chromogen-reactive-indicator composition, and to any buffer included in the composition.

Similarly, the chromogen-reactive-indicator compatible acid addition salt of the 3,3'-disubstituted benzidine derivative of the invention is an addition salt of the specific derivative (wherein X is the carbonyloxy group) and prepared by the use of an inorganic or organic acid which when combined with the derivative to form an acid addition salt of it leaves the resulting acid addition salt compatible, in that it is inert to, the just foregoing referred to constituents of a chromogen-reactive-indicator composition.

In analytical tests of the above referred to type, certain simple benzidine derivatives, such as o-dianisidine and o-tolidine, have attained wide practical use as the chromogens. In their oxidized state light absorption occurs within the wave length range of about 450 nanometers (nm), and there is found a direct relationship between the color extinction and the amount of the sugar or other component substance to be determined.

The chromogens used heretofore, however, manifest certain disadvantages. For example, the low solubility of the earlier used benzidine derivatives, being about 100 mg./liter in the reduced state and about 10 mg./liter in the oxidized state, is a drawback. Therefore, the color that they provide must be observed and recorded within a short time span. Furthermore, the color of oxidized o-dianisidine is sensitive to light. When exposed to light, its extinction can decline quickly to the extent of up to 25 percent, resulting in incorrect and widely varying results. The time required for the development of color at about 450 nm is disturbingly long in determinations where o-dianisidine and o-tolidine are used.

With them, at room temperature a color development time of between 50 to 60 minutes often is required. Then too, the tubing material used in the analytical instruments absorbs oxidized o-dianisidine and o-tolidine with its resulting discoloration, which in turn results in giving incorrect analytical data. To avoid the disturbingly long development time of the color which absorbs light in the same wave length range as o-dianisidine, a temporarily appearing color having an absorption at about 630 nm often is utilized with o-tolidine. Moreover, this color is very sensitive to variations in pH and temperature, which also influence the time for the maximum development of the color.

The studies carried out in the development of this invention to attain chromogens with properties suitable for the higher demands of modern analytical activity, resulted in the herein described new class of chromogen compounds meeting these demands and having the following general formula:

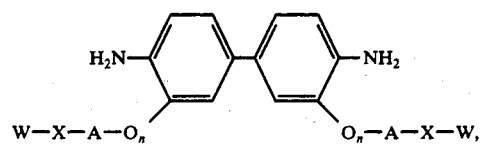

as well as their earlier herein mentioned chromogen-reactive-indicator compatible acid addition salts, and in which formula the subscript $n$ is 0 or 1, $A$ is a divalent lower alkylene chain with from 2 and beneficially at least 3 to about 7 carbons, and X and W separately are defined as recited respectively earlier above (in the second paragraph of this specification). The group —X—W is the carboxyl or sulfonic acid group, or the carboxylate or sulfonate group when W is a chromogen-reactive-indicator compatible cation other than hydrogen.

The 3,3'-disubstituted benzidine derivative in the class of chromogens used in the preparations of the invention can be obtained by various methods including different combinations of steps. Initially in each individual procedure the availability of a suitable starting material is important. These 3,3'-disubstituted benzidine derivatives are not the subject matter of the present application, but rather are that of U.S. Pat. No. 3,859,341 issued on the grandparent application Ser. No. 118,531 hereof and of U.S. Pat. No. 4,008,267 issued on the parent application Ser. No. 515,195 hereof.

Accordingly, for the applicable starting materials for, and the methods of preparing, the 3,3'-disubstituted benzidine derivatives and the acid addition salts of those of them wherein X is the carbonyloxy group, refer to U.S. Pat. No. 3,859,341 especially from column 3 line 56 to column 9 line 49. The entire content of which portion of that patent is incorporated herein by reference and considered as if appearing herein in full.

The preparation of other applicable starting materials for, and the method of preparation, of others of the 3,3'-disubstituted benzidine derivatives suitable as chromogens in the preparations of this invention, such as those wherein X is the sulfonyloxy group and $n$ is 0, refer to U.S. Pat. No. 4,008,267 from column 10 line 20 to column 12 line 8 inclusive. All of that portion of this parent application is incorporated herein by reference and considered as if appearing herein in full.

Accordingly, the 3,3'-disubstituted benzidine derivatives and acid addition salts thereof, applicable as chromogens in the color change reagent preparations comprising a chromogen-reactive-indicator of this invention are illustrated by, but not restricted to, the following:

gamma,gamma'-(4,4'-diamino-3,3'-biphenyldioxy)-dibutyric acid dihydrochloride,
gamma,gamma'-(4,4'-diamino-3,3'-biphenyldioxy)-dibutyric acid;
gamma,gamma'-(4,4'-diamino-3,3'-biphenyldioxy)-dipropane sulfonic acid and also its disodium salt,
delta,delta'-(4,4'-diamino-3,3'-biphenyldioxy)dibutane sulfonic acid,
gamma,gamma'-(4,4'-diamino-3,3'-biphenyl)dibutyric acid,
delta,delta'-(4,4'-diamino-3,3'-biphenyl)divaleric acid,
beta,beta'-(4,4'-diamino-3,3'-biphenyl)-diethane sulfonic acid and the sodium salt and the dipotassium salt of this sulfonic acid substance; and gamma,gamma'-(4,4'-diamino-3,3'-biphenyl)-dipropane sulfonic acid.

By including a 3,3'-disubstituted benzidine derivative of the class described above as the chromogen-reactive-indicator constituent of the color change reagent preparations of the invention, the resulting chromogen-reactive-indicator compositions are admirably useful in analytical procedures such as those earlier above described.

Thus, in addition to the 3,3'-disubstituted benzidine derivative as the chromogen-reactive-indicator, the color change reagent preparations of the invention comprise also a hydrogen-peroxide-oxidoreductase as which peroxidase is used, a specific oxygen-oxidoreductase for the specific material in the testing for which such composition of this invention will be used, such as glucose oxidase when testing for glucose, galactose oxidase in testing for galactose, uricase in making determinations of uric acid, pyridoxaminophosphate oxidase in determining pyridoxaminophosphate, and the specific amino acid oxidase in making determinations of a specific amino acid. These three essential constituents generally are merely dissolved in distilled water, in which usually also is included a buffer to pH 7.

In connection with these color change reagent compositions of the invention, laboratory tests were conducted by a standard method for evaluating different chromogens. Glucose was used as the control or test substance to be tested for in these tests. Hence, its corresponding specific oxidase, namely glucose oxidase, was included as the specific oxidase in the respective chromogen-reactive-indicator compositions tested, wherein the specific constituents were included in the following standard quantitative contents:

| Chromogen used | 0.2 mM (i.e. millimolar), |
| --- | --- |
| peroxidase | 300 units, |
| glucose oxidase | 3000 units, |
| phosphate buffer to pH 7 | 0.1 M, and |
| distilled water to make | 1000 ml. |

Stock or test solutions were prepared containing glucose in concentrations of 25, 50, 100, 200, 300, and 400 mg. per 100 ml.

When routinely using reagents or testing compositions according to the just above described plan, determinations of biological, protein-containing materials, for example, blood, also are made. In such cases, initially a precipitation of proteins is made, for example, with 0.33 M glycine-buffered perchloric acid to pH 2.7, after which the sample is diluted 1 part to 21. Before the final determination, this thus diluted solution is diluted further 1 part to 11 with the just above described chromogen reagent solution. Thereafter the development of color is measured at 450 nm.

When this particular dilution pattern is applied to the foregoing stock or test stem solutions, finally diluted solutions with the following respective glucose contents are obtained:

2.2, 4.3, 8.6, 13.0, and 17.3 mg. per liter.

The chromogen-reactive-indicator compositions of the invention, and the improved testing method involving their use are illustrated by, but not restricted to, the following examples:

EXAMPLE A

Chromogen Of Example 1(d)

A chromogen-reactive-indicator preparation of the foregoing standard constitution with 0.2 mM gamma,gamma'-(4,4'-diamino-3,3'-biphenyldioxy)dibutyric acid -di-HCl of Example 1(d) as a chromogen was evaluated by the foregoing standard protocol against the various glucose stock solutions. Maximum color development at 450 nm occurred within 25 minutes at 25° C. and within 15 minutes at 37° C. respectively. The solubility in water of this acid addition salt used as the new chromogen was very good, and no precipitation of chromogen occurred. Its color stability at its extinction maximum enabled reading at an optional time up to 4 hours.

For use in automatic analyzers, it is desirable that the rubber or various plastic materials forming part of the tubing should not be discolored by the chromogen-containing reagent solution. Samples of various kinds of tubings were immersed for 25 hours separately respectively in chromogen-reactive-indicator reagent compositions of the foregoing constitution, one of them having as its chromogen the product of Example 1(d) hereof, a second of them having the product of Example 3(b), and a third having o-dianisidine instead. The tube samples immersed in the reagent composition containing the product of Example 1(d) remained colorless whereas those tube samples immersed in the reagent composition containing the o-dianisidine turned brown. As to these latter, to the extent that reactions occurred between the o-dianisidine and the tube material, analyses using it yield incorrect results.

EXAMPLE B

Chromogen of Example 3(b)

A chromogen-reactive-indicator reagent preparation of the foregoing standard constitution with 0.2 mM. gamma,gamma'-(4,4'-diamino-3,3'-biphenyldioxy)dipropane sulfonic acid of Example 3(b) as its chromogen was evaluated by the foregoing standard procedure against the various glucose stock solutions. Maximum color development at 430 to 450 nm occurred within 25 minutes at 25° C. The solubility in water of the new chromogen is quite good, and thus no precipitation of it occurs. The color stability of this chromogen of Example 3(b) at extinction maximum enables reading at an optional time up to 4 hours, which was the longest period over which the test material was observed.

Like analytical tests of others of these color change reagent preparations of this invention containing any of the other 3,3'-disubstituted benzidine derivatives or an indicated acid addition salt applicable as the chromogen constituent of these preparations show that these properties exhibited by the two chromogens of Examples 1(d) and 3(b) are manifested also by the preparations of this invention including any of the other chromogens embraced by the general description of the compounds applicable as the chromogen-reactive-indicator constituent of the color change reagent preparations of this invention. Comparisons of the behavior of the commonly used benzidine derivatives o-dianisidine and o-tolidine with the chromogens applicable in the preparations of these examples of this invention show results given in the following table:

| Chromogen used | Wave length range in nm | pH value | Solubility at pH 7 in mg/liter | | Extinction decrease % after irradiation 5 min. under 10 Watt tungsten lamp | Time for color development (in minutes) | | Absorption by tubing material |
|---|---|---|---|---|---|---|---|---|
| | | | reduced (uncolored) | oxidized (colored) | | 25° C | 37° C | |
| o-dianisidine | 450 | 6.5 | 110 | 10 | 26 | 50 | 35 | + |
| o-tolidine | 430 | 6.5 | 130 | 7 | 1 | 60 | 45 | + |
| o-tolidine | 630 | 4.5 | 130 | 7 | unstable | 10 | 6 | + |
| Product of Example 1 (d) | 450 | 6.5 | 70000 | 700 | 2 | 25 | 15 | − |
| Product of Example 3 (b) | 450 | 6.5 | 12000 | 120 | 2 | 25 | 15 | − |

Except for the solubility data, the rest of the information in the foregoing table applies to each of the different chromogens identified in its first column as included separately respectively as the chromogen in a chromogen-reactive-indicator reagent preparation qualitatively and quantitatively composed as given.

While the invention has been explained by detailed description of certain specific embodiments of it, it is understood that various modifications and substitutions may be made in any of them within the scope of the appended claims which are intended also to include equivalents of the disclosed specific embodiments.

What is claimed is:

1. In an analytical test, color change reagent preparation comprising a chromogen-reactive-indicator, peroxidase, an oxygen-oxidoreductase specific to a particular substance to be tested and for which there exists a specific oxygen-oxidoreductase, the improvement which consists in using as the chromogen-reactive-indicator constituent of said preparation a 3,3′-disubstituted-benzidine derivative selected from (a) those having the general formula

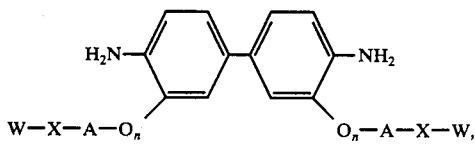

wherein X is the divalent carbonyloxy or sulfonyloxy group, W is hydrogen or another cation compatible with the aforesaid other ingredients of said reagent preparation, the subscript $n$ is 0 or 1, and (i) when X is the carbonyloxy group, A is a divalent alkylene chain with from 2 to about 7 carbons, and (ii) when X is the sulfonyloxy group, $n$ is 0 when A is the divalent alkylene chain of from 2 to about 7 carbons, and $n$ is 1 when A is straight chain trimethylene or tetramethylene, and (b) the acid addition salts of said disubstituted benzidine derivative, compatible with the aforesaid ingredients of the chromogen-reactive-indicator, when X is the carbonyloxy group.

2. The improvement in an analytical reagent preparation as claimed in claim 1, wherein the said indicator constituent is said disubstituted benzidine derivative wherein A is the carbonyloxy group.

3. The improvement in a reagent preparation as claimed in claim 2, wherein said indicator constituent is a chromogen-reactive-indicator compatible acid addition salt.

4. The improvement in a reagent preparation as claimed in claim 3, wherein said acid addition salt is such salt of gamma,gamma′-(4,4′-diamino-3,3′-biphenyldioxy)dibutyric acid.

5. The improvement in a reagent preparation as claimed in claim 4, wherein said acid addition salt is a di-hydrohalide.

6. The improvement in a reagent preparation as claimed in claim 5, wherein said di-hydrohalide is the di-hydrochloride.

7. The improvement in a reagent preparation as claimed in claim 2, wherein said indicator constituent is gamma,gamma′-(4,4′-diamino-3,3′-biphenyldioxy)dibutyric acid.

8. The improvement in an analytical reagent preparation as claimed in claim 1, wherein the said indicator constituent is said disubstituted benzidine derivative wherein A is the sulfonyloxy group.

9. The improvement in a reagent preparation as claimed in claim 8, wherein said indicator constituent is gamma,gamma′-(4,4′-diamino-3,3′-biphenyldioxy)propane sulfonic acid.

10. In the analytical method for testing in an aqueous test sample for the presence of an organic substance for which there is a specific oxygen-oxidoreductase, by use of a chromogen-reactive-indicator preparation which contains peroxidase and the oxygen-oxidoreductase for said substance, and in which method hydrogen peroxide forms during the analytical reaction, the improvement which comprises using as the chromogen-reactive-indicator constituent of said preparation the chromogen-reactive-indicator used in the color change reagent preparation of claim 1.

11. The improvement in the analytical method as claimed in claim 10, wherein said indicator constituent is said disubstituted benzidine derivative wherein A is the carbonyloxy group.

12. The improvement in the analytical method as claimed in claim 11, wherein said indicator constituent is a chromogen-reactive-indicator compatible acid addition salt.

13. The improvement in the analytical method as claimed in claim 12, wherein said acid addition salt is such salt of gamma,gamma′-(4,4′-diamino-3,3′-biphenyldioxy)dibutyric acid.

14. The improvement in the analytical method as claimed in claim 13, wherein said acid addition salt is a dihydrohalide.

15. The improvement in the analytical method as claimed in claim 14, wherein said di-hydrohalide is the dihydrochloride.

16. The improvement in the analytical method as claimed in claim 11, wherein said indicator constituent is gamma,gamma′-(4,4′-diamino-3,3′-biphenyldioxy)dibutyric acid.

17. The improvement in the analytical method as claimed in claim 10, wherein said indicator constituent is said disubstituted benzidine derivative wherein A is the sulfonyloxy group.

18. The improvement in the analytical method as claimed in claim 17, wherein said indicator substituent is gamma,gamma′-(4,4′-diamino-3,3′-biphenyl)-propane sulfonic acid.

* * * * *

UNITED STATES PATENT AND TRADEMARK OFFICE
CERTIFICATE OF CORRECTION

PATENT NO. 4,066,408

DATED January 3, 1978

INVENTOR(S) Nils Åke Jönsson, Ferenc Merényl and Lars-Erik Westlund

It is certified that error appears in the above-identified patent and that said Letters Patent are hereby corrected as shown below:

Column 2 line 66, "of" should read -- or --.

Signed and Sealed this

Twenty-fifth Day of December 1979

[SEAL]

Attest:

SIDNEY A. DIAMOND

Attesting Officer

Commissioner of Patents and Trademarks